US006276365B1

United States Patent
Stelzenmuller

(10) Patent No.: US 6,276,365 B1
(45) Date of Patent: Aug. 21, 2001

(54) EMERGENCY SUPPORT FOR STABILIZING INDIVIDUAL LIMBS OR BODY PARTS

(76) Inventor: Wolfgang Stelzenmuller, Hirtengasse 9-11, D-63263, Neu-Isenburg (DE)

( * ) Notice: Subject to any disclaimer, the term of this patent is extended or adjusted under 35 U.S.C. 154(b) by 0 days.

(21) Appl. No.: 09/319,024
(22) PCT Filed: Sep. 25, 1998
(86) PCT No.: PCT/EP98/06110
  § 371 Date: Jul. 26, 1999
  § 102(e) Date: Jul. 26, 1999
(87) PCT Pub. No.: WO99/16392
  PCT Pub. Date: Apr. 8, 1999

(30) Foreign Application Priority Data

Sep. 28, 1997 (DE) .............................. 197 42 833
Feb. 20, 1998 (DE) .............................. 198 07 112

(51) Int. Cl.[7] .................................................. A61B 19/00
(52) U.S. Cl. .............................. 128/869; 128/870; 5/628
(58) Field of Search .................................. 128/845, 846, 128/869, 870, 882; 5/628, 913; 602/5, 20, 21, 26

(56) References Cited

U.S. PATENT DOCUMENTS 3,745,998 * 7/1973 Rose .................................. 128/89 R
3,762,404 * 10/1973 Sakita .......................... 128/DIG. 20
4,885,811 * 12/1989 Hayes .................................. 128/870
5,626,150 * 5/1997 Johnson .............................. 128/870

* cited by examiner

Primary Examiner—Michael A. Brown
(74) Attorney, Agent, or Firm—Fulbright & Jaworski LLP

(57) ABSTRACT

Emergency support for stabilization of individual limbs or body parts for transport or for performance of surgical-treatment measures, including a granulate-filled cushion (1) which is provided with a valve (2) for purposes of alternating evacuation and filling, and which allows at least partial surrounding of the limb or body part, made of two lengths of airtight flexible material which are connected on their edges, in which within the cushion interior which contains the granulate there are chokes (7) to prevent the free flow of granulate and the cushion in the middle area of its outer surface which faces away from the body after application is provided with a Velcro strip border (8) as part of a Velcro-pile connector, for fixation on a solid structure. The cushion on the inside and on the outside is provided with Velcro or pile spots (9, 10) of a Velcro-pile connector for fastening of another auxiliary element provided with a corresponding opposite border, especially a chin support and/or the filter system of a respirator.

4 Claims, 8 Drawing Sheets

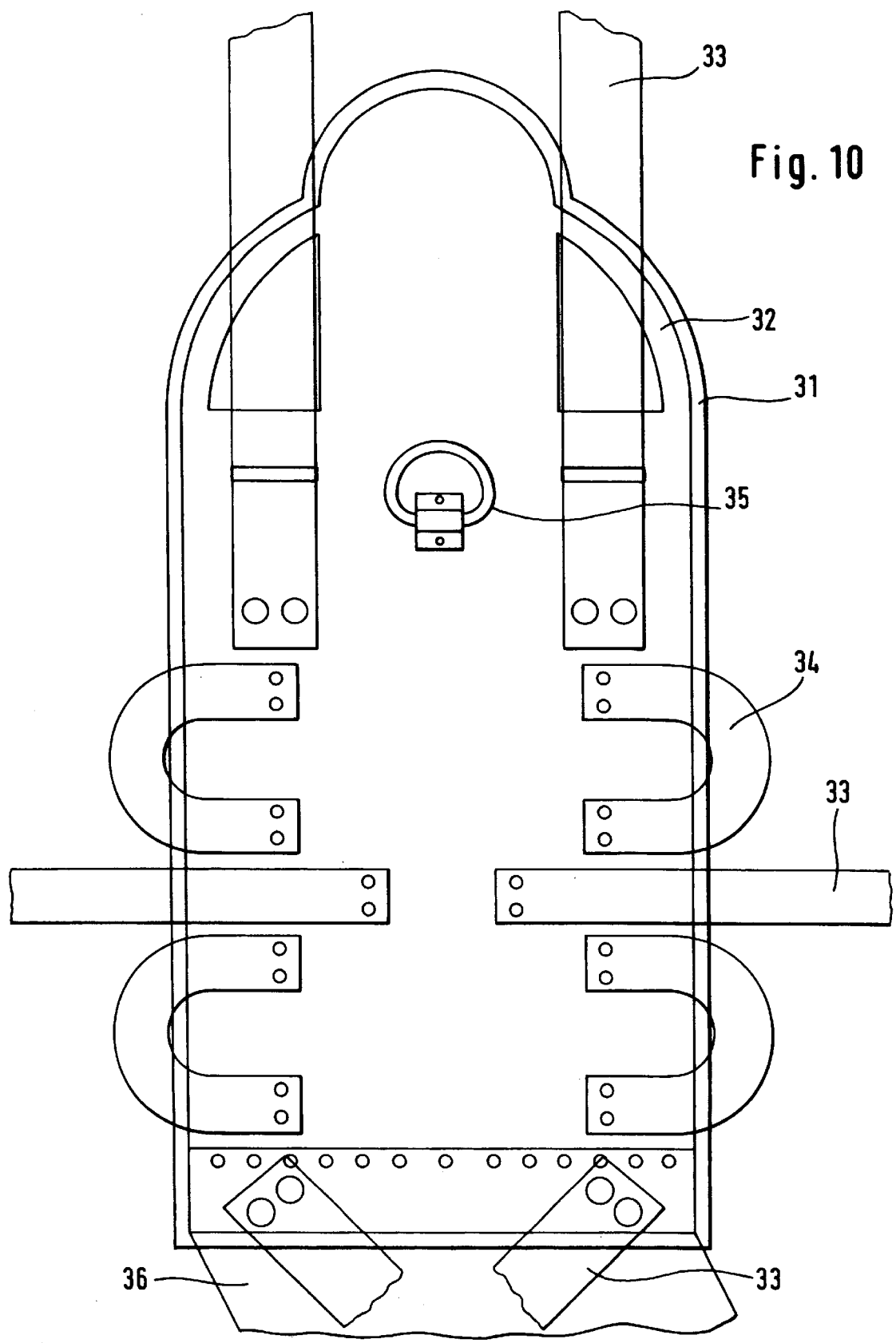

US 6,276,365 B1

EMERGENCY SUPPORT FOR STABILIZING INDIVIDUAL LIMBS OR BODY PARTS

The immobilization of an accident victim in rescue at the accident site, for example from a motor vehicle or in impassable terrain, and for his transport to the hospital is, as in the past, a problem which has not been satisfactorily solved. Especially in cases in which skull, nape of the neck or thoracic vertebral injuries must be assumed, the prevention of changes in position until the type of treatment has been definitively clarified is generally of critical importance. Various embodiments of so-called rescue splints are known and are in use; they are however to some extent very unwieldy and thus unmanageable and difficult to apply, in all cases for application however they require prior rescue of the injured party which is generally associated with major changes in his position.

The corresponding applies to a series of surgeries in the head and neck area, for example, performing a tracheotomy during which a perfectly stable location must be ensured for a longer time with perfectly reliable immobilization of the neck area and head. The belt systems used for this purpose in operating rooms cannot adequately meet this requirement due to their flexibility.

A fixed dressing for the cervical spinal column has been disclosed for example in DE-GM G 83 12 991; it consists of several interconnected, tube-like sleeves which are delineated against one another, which are filled with a granulate, and after application in a manner which essentially surrounds the head and neck area, which can be evacuated so that the head and neck area are embedded securely in the sleeves. This known fixed dressing has a series of major defects. One defect lies especially in the mutual delineation of the individual sleeves which on the one hand not only essentially hinders, but almost prevents both evacuation in one step with the corresponding delay of the application of the fixed dressing, and on the other hand also the transfer of granulate from one sleeve into the adjacent one and thus its adaptation to the form dictated by the situation. In addition, the emergency support as a result of the connection of the individual sleeves over its entire length completely surrounds the supported body part, but especially the neck area of the patient and thus precludes access for interventions which may be necessary to save life, for example, a tracheotomy. For use in emergency situations which on the one hand require extraordinary flexibility, prompt and easy handling and access to the neck area without significant loss of the support effect, the known sleeve thus appears unsuited and has therefore not been accepted in either emergency or in-patient medical practice.

Accordingly the object of this invention is to devise an emergency support which allows simple application even under difficult ambient conditions and perfectly safe stabilization of the location of the supported body region with good access as required to sensitive areas of the body, especially the neck area.

This object is achieved with an emergency support with the features given in claim 1.

The invention devises an emergency support which in its totality can be evacuated in one step and therefore can be quickly and easily brought into its hard shell form, on the one hand preventing the flow of granulate from one area into other areas, i.e. guaranteeing high stability of shape even under difficult working conditions, but it being possible without major problems so that especially for application the adaptation to the necessities resulting from the respective local and personal situations is easily possible. The emergency support as claimed in the invention can be caused to assume any form and thus it can be moved into position using extremely small open spaces or openings and adapted to the shape of the body, and afterwards consolidated with this contour adapted to the shape of the body with a single evacuation process to form a rigid and closed support. Application of the support can thus be done even under difficult ambient conditions or in impassable terrain so that changes in position can be for the most part precluded from the start of rescue of the injured party to his in-patient admission.

Other details of the invention are explained below using the attached drawing.

Figure 7:
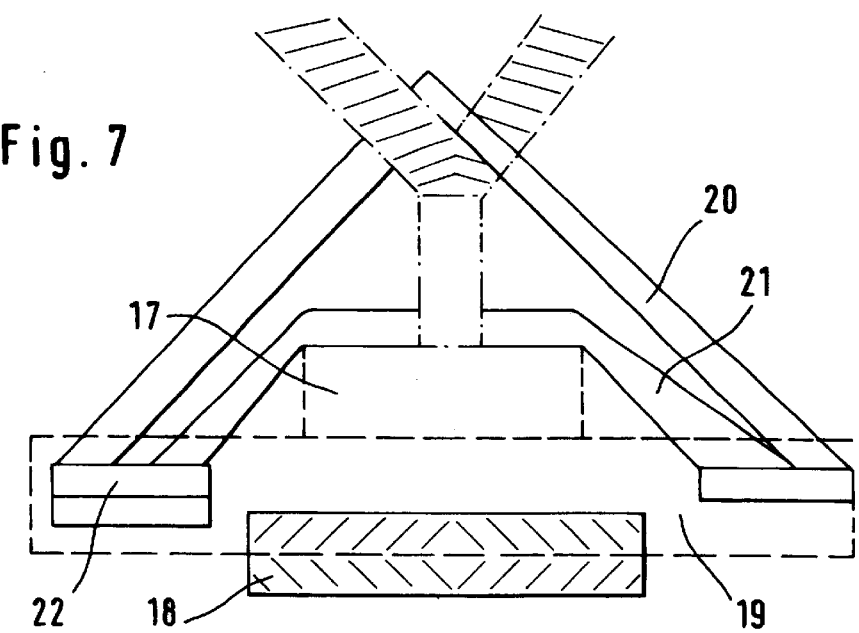
Figure 8:
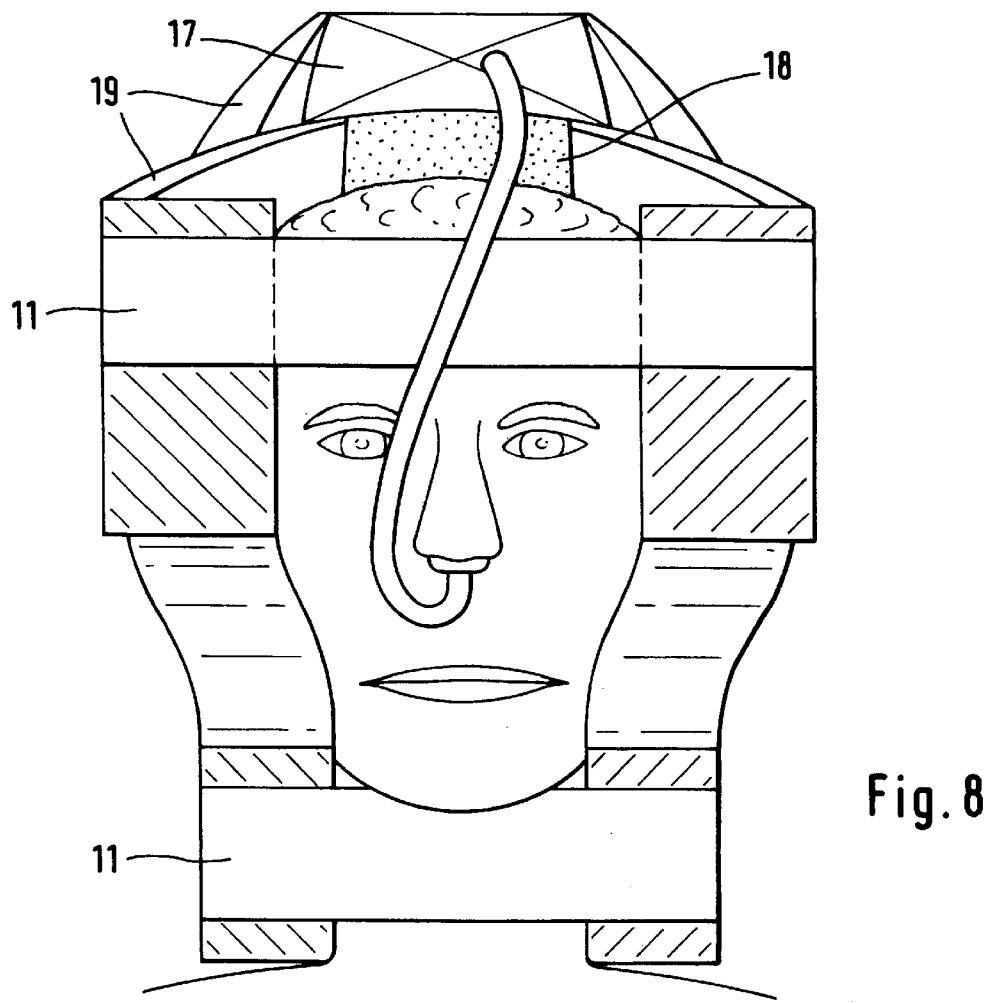
Figure 11:
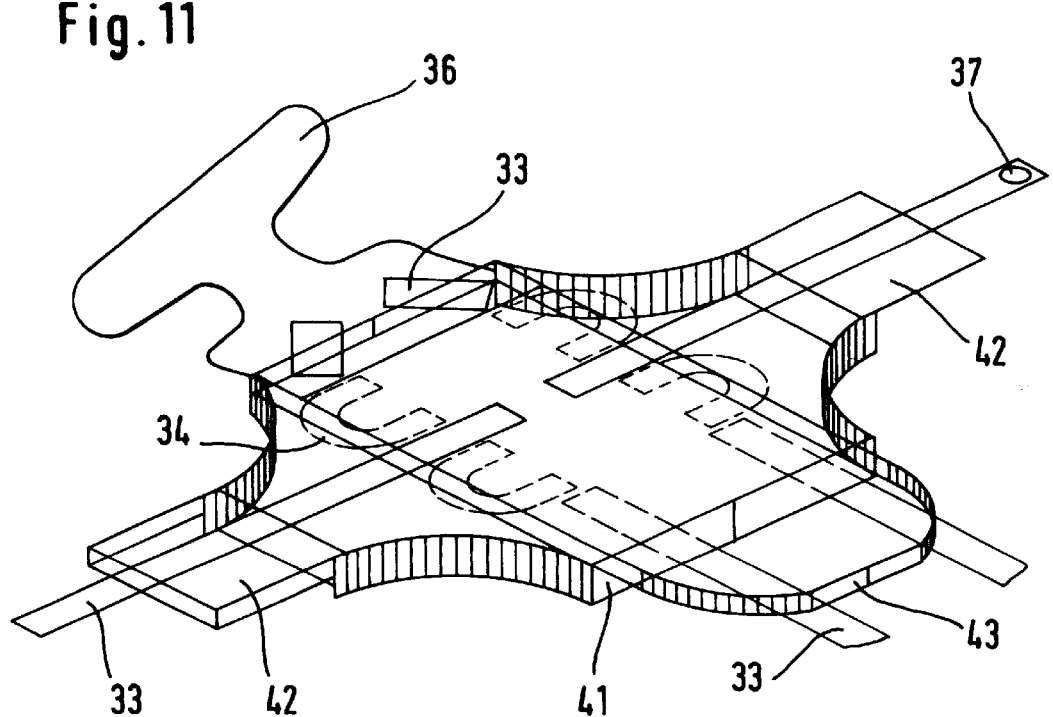
Figure 9:
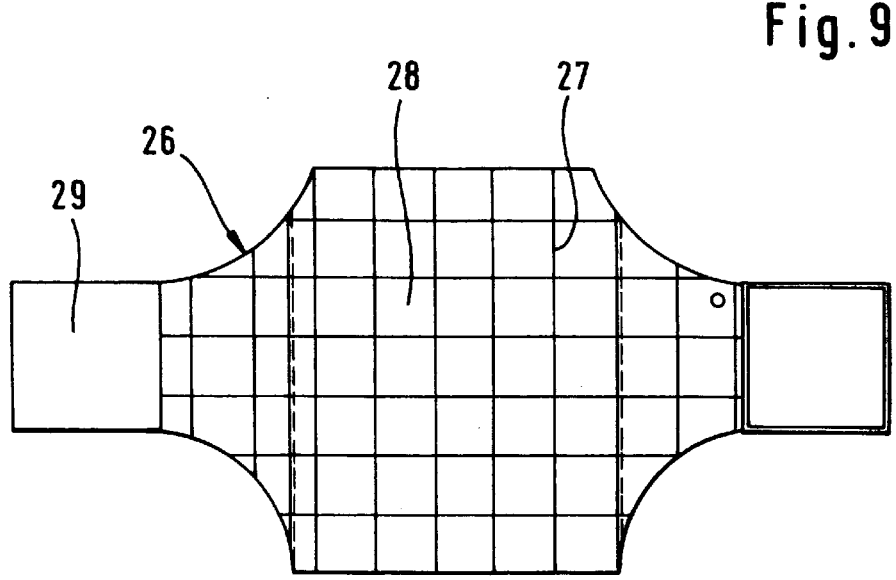
Figure 12:
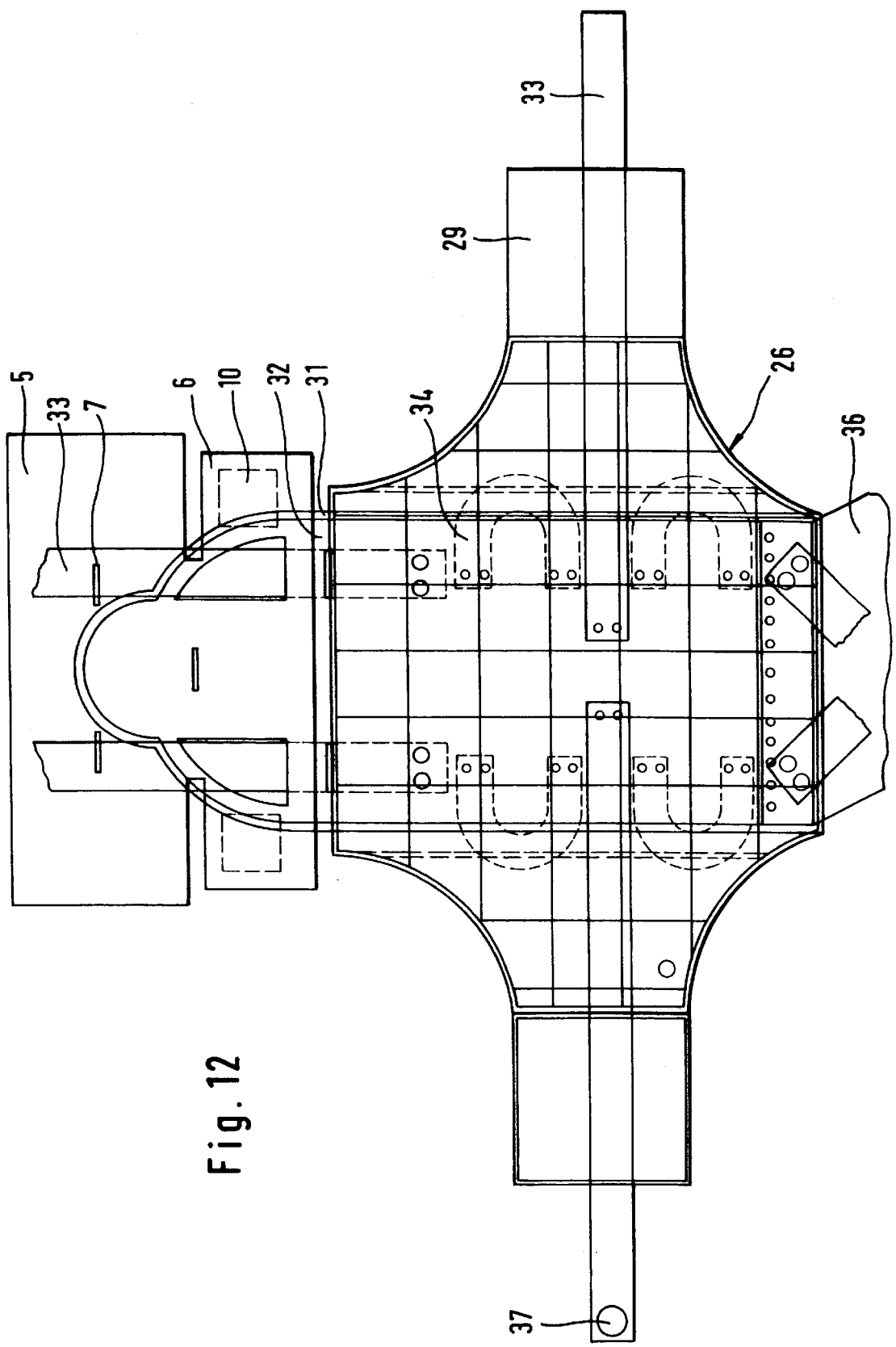
Figure 13:
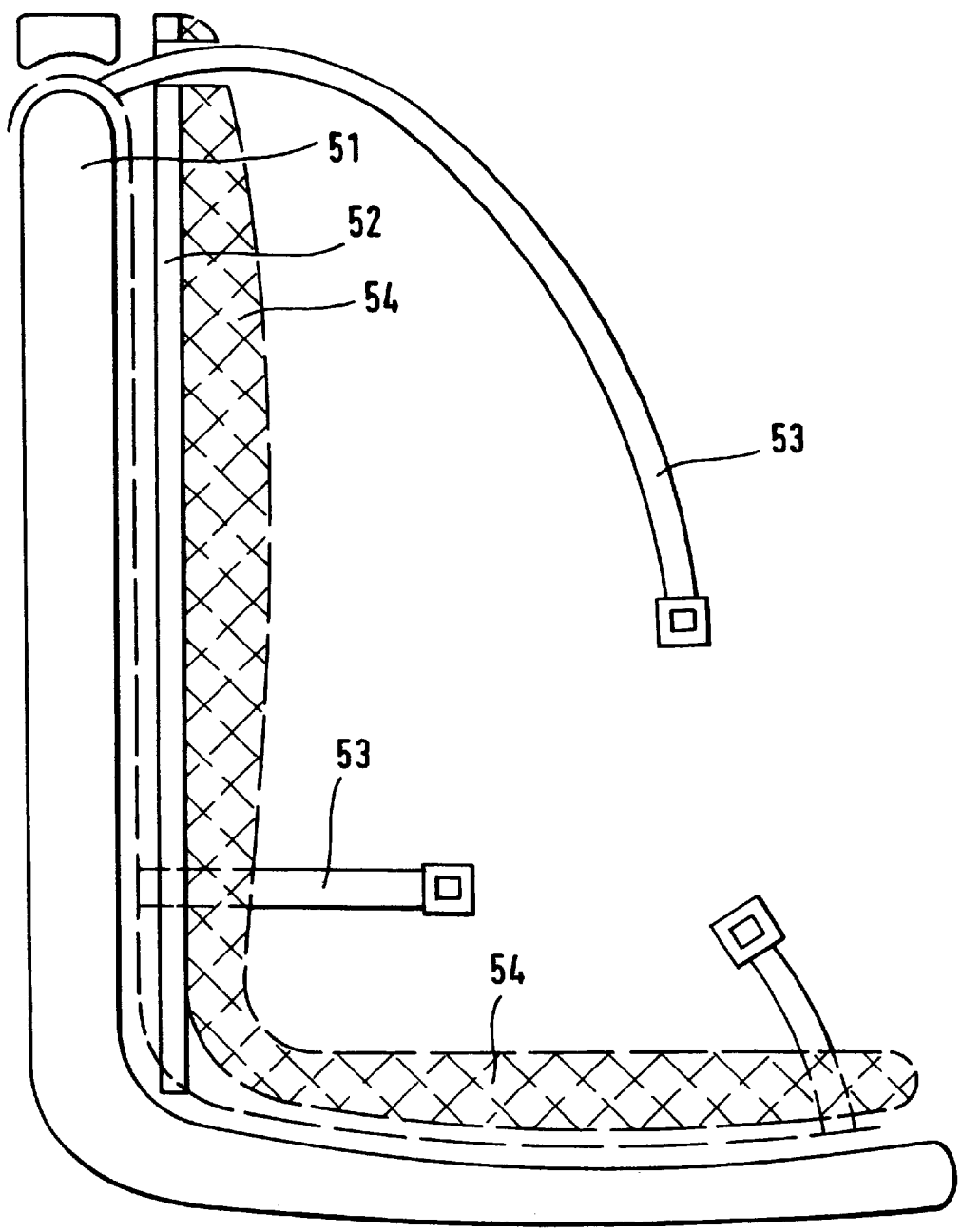
Figure 14:
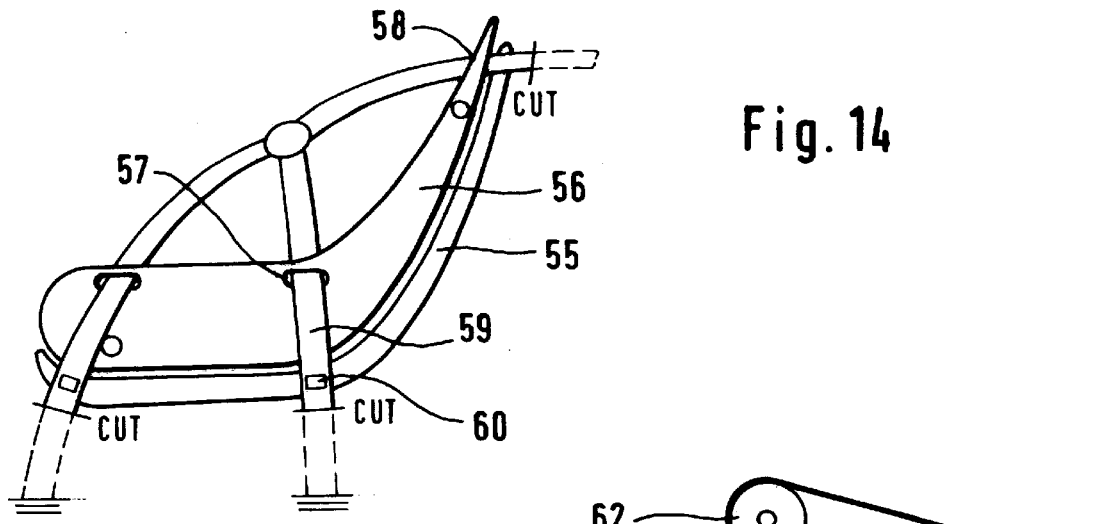
Figure 15:
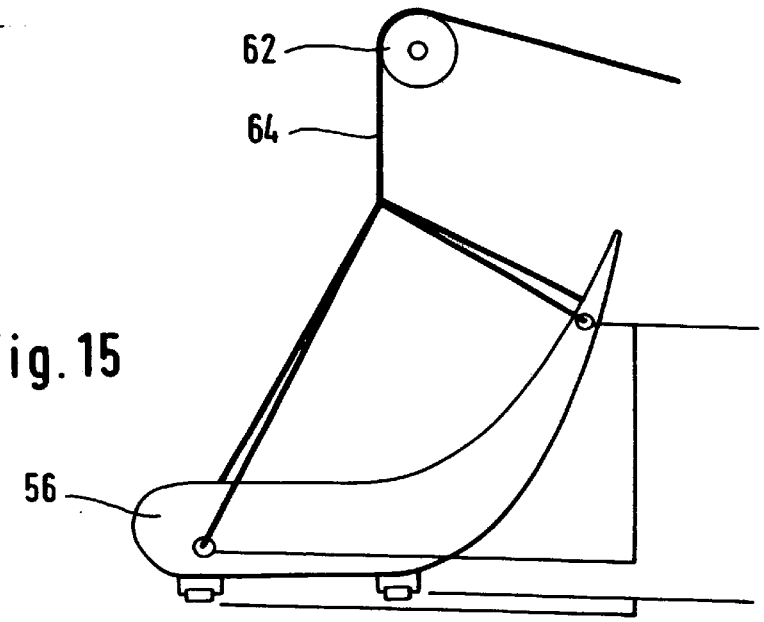
Figure 16:
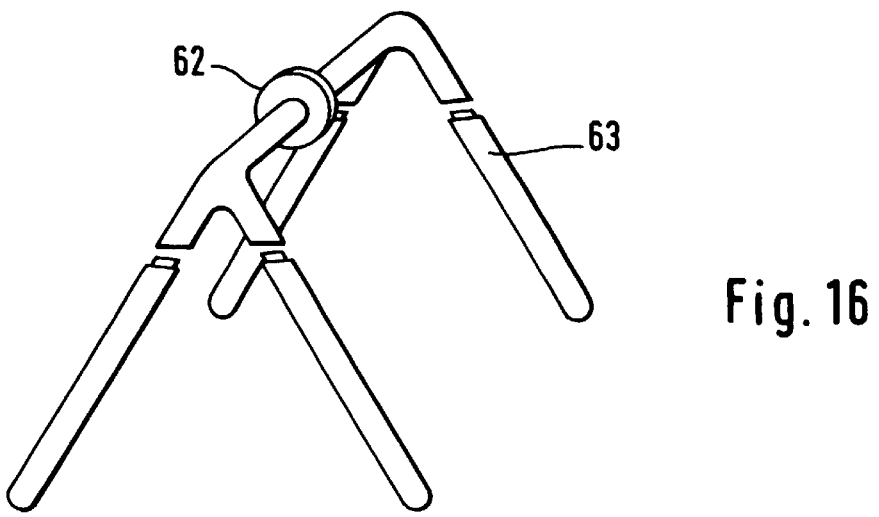

FIG. 7 shows a schematic of an attachment belt for the filter system of a respirator FIG. 8 shows a view of the head with the emergency support applied with a filter system for a respirator FIG. 9 shows a view of a thoracic emergency support which is used to stabilize the chest and lumbar vertebral area FIG. 10 shows a rear view of a stretcher or rescue plate for forming a rescue device FIG. 11 shows a schematic perspective of a cover for a rescue plate with a thoracic emergency support, FIG. 12 shows a complete reproduction of a rescue device FIG. 13 shows a schematic section of one embodiment of a motor vehicle seat with an integrated rescue plate FIG. 14 shows a schematic section of a motor vehicle seat which forms the solid structure of a rescue system at the same time FIG. 15 shows a perspective of a view of a lifting frame for lifting the rescue system from a motor vehicle FIG. 16 shows a schematic of the lifting process.

Figure 1:
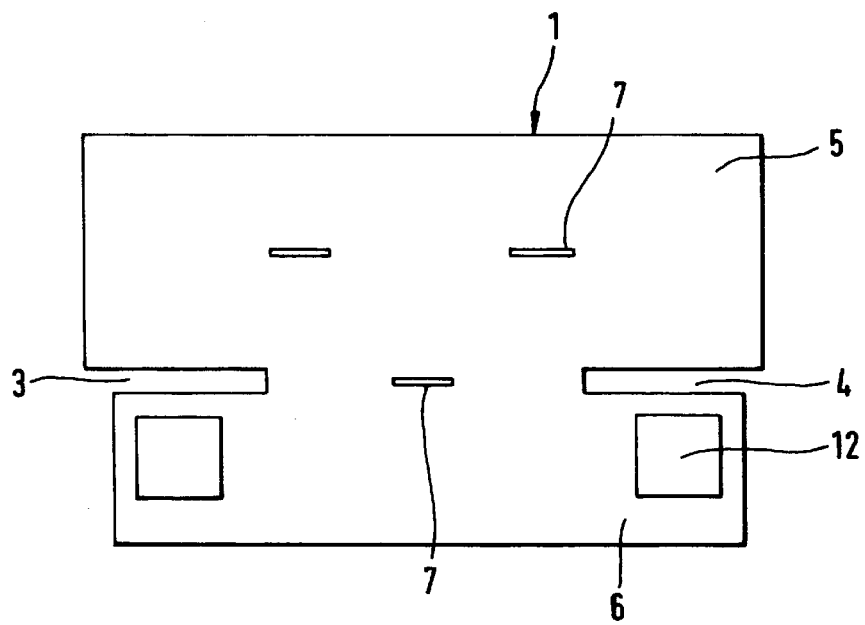
FIG. 1 shows a view of a cervical emergency support which is used for stabilization of the head area and the area of the nape of the neck
Figure 2:
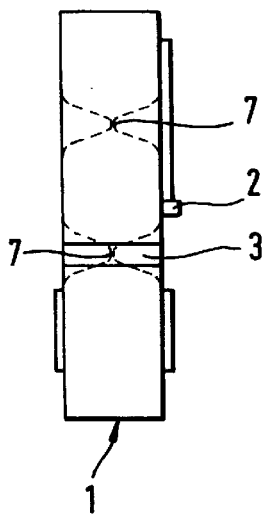
FIG. 2 shows a view from the side of FIG. 1

FIGS. 1 to 6 show a cervical emergency support which is used for stabilization of the area of the head and nape of the neck of an individual and which includes essentially a granulate-filled cushion 1 which is provided with a valve 2 for purposes of alternating evacuation and filling, made of two lengths of airtight flexible material which are connected on their edges. In the case of an embodiment which reproduces a cervical cushion the cushion is divided by means of two lateral, aligned notches 3, 4 into two segments 5, 6, of which segment 5 is used to surround the skull and the other segment 6 is used to surround the nape-neck area, in the area between the notches 3, 4 there being one and in the larger of the two segments 5 two more cross sectional narrowings aligned with one another in the form of dash-like welds 7 as drip barriers, by which the cushion is divided into several zones, in this exemplary case, three, between which flow of granulates is prevented. In this way, by the corresponding external pressure the granulate is pressed from one zone into the other and the shape is imparted to the cushion which is required for the individual case, for example, when applied in a space with restricted motion, and which it retains during further activity as a result of the prevention of free flow caused by the drip barriers at least essentially during the critical application phase. FIG. 2 which schematically shows the weld 7 clearly indicates that a narrowing of the flow cross section which far exceeds the length of the weld seam is achieved by the connection as a result of the dramatic tapering around the seam.

Figure 3:
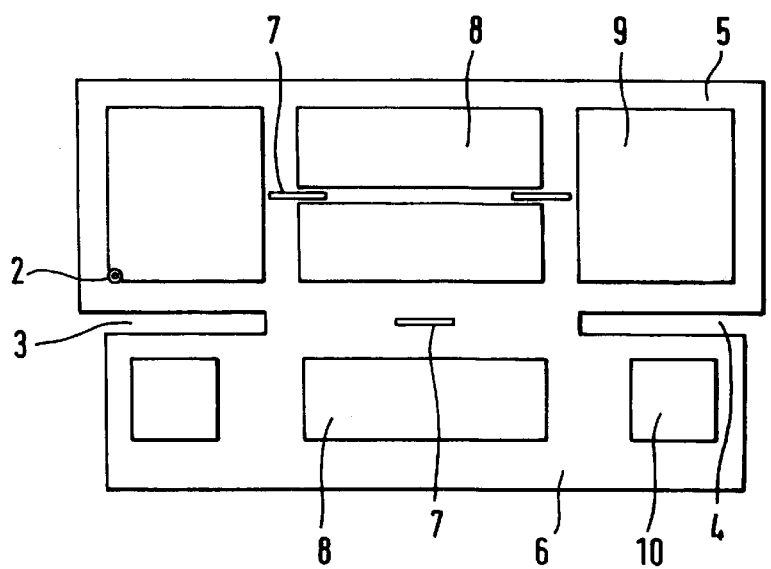
FIG. 3 shows a rear view of the emergency support shown in FIG. 1
Figure 6:
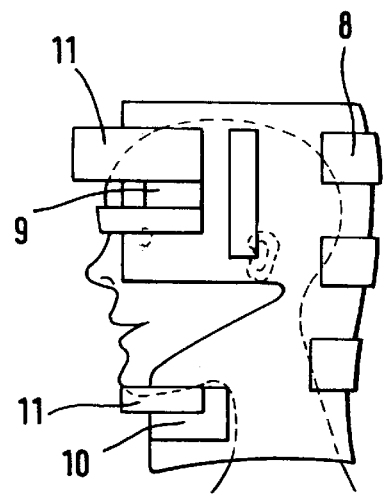
FIG. 6 shows a side view of a head with the emergency support

The cushion 1—see especially FIG. 3—in the middle area of its outer surface which faces away from the body after application is provided with a Velcro strip border as part of a Velcro-pile connector, said border consisting of three spots in the exemplary case; the connector can then be used for direct fixation of the cushion 1 on a solid structure which is provided with a pile border or for attachment of a magnetic, adhesive PVC or similar adhesive film which bears the pile border; using this film it can be fixed on a solid structure which has a corresponding surface, for example an operating table or a dentist's chair. It has been found that by applying only one evacuatable granulate sleeve sufficient immobilization of the body or individual body parts cannot be achieved, rather twisting is possible which may be dangerous and which is undesirable in critical cases and which can be reliably prevented by stabilizing the cushion by means of a solid structure, so that only in this way is the desired objective of sufficient immobilization of the body achieved. In this case great flexibility is achieved by the possibility of attaching adhesive films which work in a different way such that any solid structure can be used which may be present, i.e. for example in an emergency an available metal or plastic plate or in in-patient or out-patient operation the existing operating table or treatment chair. This greatly expands the possible applications of the emergency support.

Other adhesive spots, for example Velcro spots 9, 10, on the outside of the cushion 1 are used to attach (pile) tension bands 11 over the forehead, eye and chin part and thus to further stabilize the head in the cushion which surrounds it.

Figure 4:
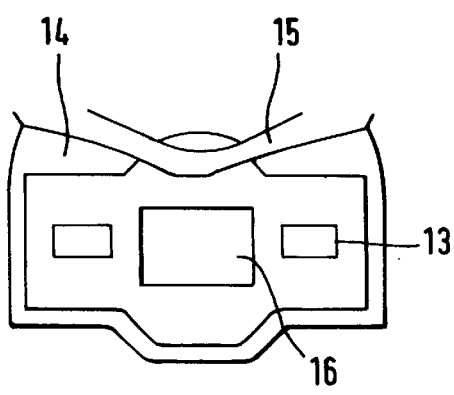
FIG. 4 shows a view of a chin support.
Figure 5:
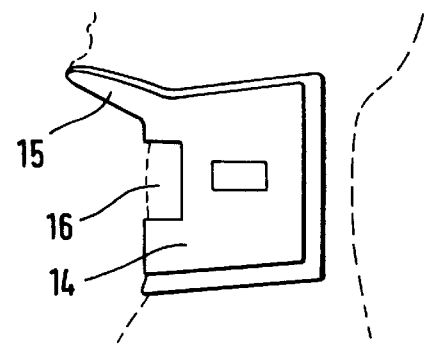
FIG. 5 shows a view from the side of FIG. 4.

Furthermore, see FIG. 1, the cushion on its inside is provided with pile spots 12 of a Velcro-pile connector for attachment of the chin support 14 which bears the corresponding Velcro spot 13 of the connector and which is shown in FIGS. 4 and 5. In this way it is securely incorporated into the overall arrangement, due to the concave arch of the chin plate 15 rotational stabilization of the head and in conjunction with fixing the cushion on a solid structure its complete immobilization being achieved. In addition the chin support which rests against the chest area of the body can itself be regarded as a solid structure which in conjunction with the skull which acts via the chin plate 15 provides for immobilization of the critical cervical vertebral area or at least contributes significantly to its immobilization. The chin support in its area underneath the chin plate 15 is provided with a window 16 through which diagnostic or first aid measures which may be necessary in the neck area, therefore for example feeling the carotid pulse, for performing a tracheotomy or the like, can be undertaken.

The (Velcro) adhesive spot 9 or a correspondingly separate adhesive spot is furthermore used—see FIG. 7 and 8—for fixing the filter system 17 of a respirator, for which purpose there is a pile band 19 which is provided with a head cushion 18 and on which surface facing away from the head cushion two pile bands 20, 21 are sewn permanently on one side in the exemplary case; a Velcro spot 22 is attached to fix the bands on the opposite side. To attach the filter first of all the pile band 19 which bears the head cushion 18 is stretched over the head and fixed on the spots 9 of the cushion 1 and afterwards the parts of the filter device are attached by means of the bands 20, 21 by fixation against the Velcro spot 22.

The emergency support shown in FIG. 9 is used to stabilize the thoracic and lumbar vertebral area and consists of a cushion 26 with an essentially cruciform outline which is divided into fields 28 by quilting or weld seams 27 in the manner of a quilt and is provided with side clips 29 which bear on their two surfaces on alternating sides Velcro and pile spots of a Velcro-pile connector. Otherwise it has one border (not shown) which corresponds to the spots 8 for fixation on a solid structure which—see FIG. 10—can be formed for example by a plastic, preferably Kevlar-Aramid, rescue plate 32 or stretcher which is coated with a velvet border 31 and on which there are strands of a six-point belt 33 with a length which makes it possible to surround the cushion including the supported patient, furthermore carrying straps 34 and an eye 35 for hooking a crane hook. On the rescue plate 32 there is furthermore an essentially T-shaped or double T-shaped pelvic cloth which can be pulled forward for rescue and transport from underneath through the crotch of the patient and can be fixed there together with the belts 33.

One modification of the embodiment of a rescue device shown in FIGS. 9 and 10 is shown in FIG. 11. In this case the essentially cruciform thoracic support and the rescue plate are provided with covers 41, 43 which bear the pile or Velcro border and which are connected or can be connected to one another, the cover 41 which surrounds the cruciform thoracic support bearing the side clips 29 which bear on their two surfaces on alternating sides Velcro and pile spots of a Velcro-pile connector, while the cover 43 which surrounds the rescue plate has openings for passage of the belts 33, the carrying loops 34, the crane eye 35 and the pelvic cloth 36. The belts preferably end in a central lock 37.

FIG. 12 shows in its totality the rescue device which allows perfect immobilization of an injured individual and his largely risk-free rescue itself using a mechanical rescue device, for example, an available shop or motor vehicle crane with hooks which are suspended in the crane eye 35, whereupon the patient who has been stabilized on the rescue plate by means of the cervical and the thoracic emergency supports 1, 26 which are fixed thereon, with chin support 14 and tension clips 29 and 42 in conjunction with the pelvic cloth 36 and the six-point belt, can be lifted mechanically even from a difficult position without the need to fear twisting or especially movement in the area of the spinal column.

In the case of the embodiment shown in FIG. 13, the solid structure is formed by a plate 52 which is integrated in a motor vehicle seat 51, the plate 52 which is made for example of Kevlar-Aramid or glass fiber material on the one hand having a form which corresponds to the seat economy, furthermore provided with the cushioning 54 which is conventional in seats and with rescue belts 53 which are housed in the conventional position of seat use at a site suitable for this purpose, i.e. a site which does not adversely affect sitting comfort, for example in cavities (hidden) which are provided especially for this purpose in the cushioning 54 of the rescue plate 52 or in the motor vehicle seat 51. In this case rescue of an individual from a wrecked motor vehicle becomes extremely simple and essentially without changing the position of the (injured) individual in such a way that first of all the individual is fixed against the plate 52 by means of the rescue belts which are cut out of the cushioning, afterwards the safety belt which is conventional in motor vehicle and which holds the individual securely on the motor vehicle seat is cut at any accessible location and the connection which holds the rescue plate 52 on the seat 51 is released and the rescue plate 51 together with the individual fixed thereon are lifted out of the vehicle.

Instead of a sandwich-like connection of the rescue plate to the motor vehicle seat, in the manner shown schematically in FIG. 14, the seat shell 55 itself is used as the solid structure of the rescue system and in the manner described using FIG. 13 it can be equipped with a separate rescue belt, at which location however the safety belts installed permanently in the motor vehicle can be made useful, such that the seat shell 55 or the plate 56 connected to it have slits 57, 58 for passage of the belts 59 which are provided, on the side of the seat 55 away from the user or the plate 56, with fittings 60 which make it possible to fix the ends of the belt on the motor vehicle seat or the plate or to connect them to one another. In this case, in a rescue situation it is simply necessary to cut the belt guided through the slit between the attachment fittings and their attachment site in the motor vehicle, with the fittings 60 to hang the belt in corresponding receivers attached to the motor vehicle seat—not visible—and to re-tension the belt by means of the tensioning means which is integrated generally in the front belt lock in order to release the injured individual cramped in the motor vehicle and to fix him immovably on the solid structure—the motor vehicle seat or plate. To further simplify the rescue activities, in the cases in which the seat is used as the solid structure of the rescue system the seat is feasibly attached to the motor vehicle floor by means of quick-action closures.

Accordingly, rescue takes place, optionally after opening the roof, see FIGS. 15 and 16, with the aid of a lifting frame 63 which has a block 62, which is seated on the vehicle or traverses it, by means of a tackle line 64 which is hung in the seat.

What is claimed is:

1. Emergency support for stabilization of individual limbs or body parts for transport or performance of surgical-treatment measures, comprising a granulated-filled cushion having a valve for purposes of alternating evacuation and filling, said cushion allowing at least partial surrounding of a limb or body part, said cushion comprising two connected lengths of airtight, flexible material wherein a cushion interior containing the granulate has baffles or chokes to prevent free granulate flow and wherein the cushion has a middle area of an outer surface which faces away from the limb or body part, said middle area having a hook and pile strip border as part of a hook and pile connector, for direct fixation on a solid structure having a hook and pile border or for attachment of a magnetic or adhesive film which bears the hook and pile border, wherein said film can be fixed on a structure the cushion being divided by means of lateral, aligned notches into first and second segments, said first segment adapted to surround a skull and said second segment adapted to surround a nape-neck area, and wherein the area between the notches has a cross sectional narrowing which prevents free flow of the granulate.

2. Emergency support as claimed in claim 1, wherein the cushion on an inside surface of the second segment which surrounds the nape-neck area and on an outside surface of the first segment which surrounds the skull is provided with hook and pile spots of a hook and pile connector for detachable fastening of another auxiliary device having a corresponding opposite hook and pile border.

3. Emergency support as claimed in claim 2, further comprising a head cushion having a hook and pile band which can be fixed at corresponding hook and pile spots of the cushion, wherein a surface facing away from the head cushion has at least one band sewn permanently on one side and a hook and pile spot disposed on an opposite side, and wherein the auxiliary device comprises a filter system of a respirator, said filed system being detachably fastenable to said head cushion.

4. Emergency support as claimed in claim 2, wherein the auxiliary device comprises a chin support having a chin plate with a window for performing diagnostic or first aid measures.

* * * * *